United States Patent
Choi et al.

(10) Patent No.: US 9,941,477 B2
(45) Date of Patent: Apr. 10, 2018

(54) COMPOUND FOR ORGANIC PHOTOELECTRIC DEVICE AND ORGANIC PHOTOELECTRIC DEVICE, IMAGE SENSOR AND ELECTRONIC DEVICE INCLUDING THE SAME

(71) Applicant: Samsung Electronics Co., Ltd., Suwon-si, Gyeonggi-do (KR)

(72) Inventors: Hyesung Choi, Seoul (KR); Tadao Yagi, Hwaseong-si (KR); Rie Sakurai, Suwon-si (KR); Gae Hwang Lee, Seongnam-si (KR); Seon-Jeong Lim, Yongin-si (KR); Xavier Bulliard, Seongnam-si (KR); Sung Young Yun, Suwon-si (KR); Dong-Seok Leem, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/358,726

(22) Filed: Nov. 22, 2016

(65) Prior Publication Data
US 2017/0148994 A1    May 25, 2017

(30) Foreign Application Priority Data
Nov. 24, 2015    (KR) .......................... 10-2015-0164996

(51) Int. Cl.
*H01L 51/00* (2006.01)
*C07D 409/06* (2006.01)
(Continued)

(52) U.S. Cl.
CPC ........ *H01L 51/0061* (2013.01); *C07D 409/06* (2013.01); *C07D 421/06* (2013.01);
(Continued)

(58) Field of Classification Search
CPC ............... H01L 27/307; H01L 27/1461; H01L 27/1464; H01L 27/14645; H01L 27/14667;
(Continued)

(56) References Cited

U.S. PATENT DOCUMENTS 6,300,612 B1    10/2001    Yu
7,129,466 B2    10/2006    Iwasaki
(Continued)

FOREIGN PATENT DOCUMENTS

DE    10-038436 A1    3/2002
EP    3026722 A1    6/2016
(Continued)

OTHER PUBLICATIONS

Satoshi Aihara et al. "Stacked Image Sensor With Green- and Red-Sensitive Organic Photoconductive Films Applying Zinc Oxide Thin-Film Transistors to a Signal Readout Circuit". IEEE Transactions on Electron Devices, vol. 56, No. 11. Nov. 2009. pp. 2570-2576.
(Continued)

*Primary Examiner* — Roy Potter
(74) *Attorney, Agent, or Firm* — Harness, Dickey & Pierce, P.L.C.

(57) ABSTRACT

A compound for an organic photoelectric device is represented by Chemical Formula 1, and an organic photoelectric device, an image sensor and an electronic device include the same.

23 Claims, 7 Drawing Sheets

(51) Int. Cl.

| | |
|---|---|
| *C07D 421/06* | (2006.01) |
| *H01L 51/52* | (2006.01) |
| *H01L 27/146* | (2006.01) |
| *H01L 27/28* | (2006.01) |
| *H01L 27/30* | (2006.01) |
| *H01L 51/44* | (2006.01) |

(52) U.S. Cl.
CPC .......... *H01L 51/006* (2013.01); *H01L 51/525* (2013.01); *H01L 27/14621* (2013.01); *H01L 27/288* (2013.01); *H01L 27/307* (2013.01); *H01L 51/0052* (2013.01); *H01L 51/0062* (2013.01); *H01L 51/0067* (2013.01); *H01L 51/44* (2013.01)

(58) Field of Classification Search
CPC ............. H01L 27/14694; H01L 51/424; H01L 51/0061; H01L 51/006; H01L 51/525; H01L 27/14621; H01L 51/0067; H01L 51/0062; H01L 51/44; H01L 51/0052; H01L 27/288; Y02E 10/549; C07D 409/06; C07D 421/06
See application file for complete search history.

(56) References Cited

U.S. PATENT DOCUMENTS

| | | | |
|---|---|---|---|
| 7,973,307 | B2 | 7/2011 | Rand et al. |
| 8,035,708 | B2 | 10/2011 | Takizawa et al. |
| 8,426,727 | B2 | 4/2013 | Pfeiffer et al. |
| 8,525,577 | B2 | 9/2013 | Yofu et al. |
| 2007/0012955 | A1 | 1/2007 | Ihama |
| 2011/0074491 | A1* | 3/2011 | Yofu ........................ H01L 51/06 327/514 |
| 2012/0313088 | A1 | 12/2012 | Yofu et al. |
| 2016/0149132 | A1 | 5/2016 | Lim et al. |

FOREIGN PATENT DOCUMENTS

| | | |
|---|---|---|
| WO | WO-02-21611 A1 | 3/2002 |
| WO | WO-2006/128818 A1 | 12/2006 |

OTHER PUBLICATIONS

Henry Irving Kohn et al. "On a New Aerobic Metabolite Whose Production by Brain is Inherited by Apomorphine, Emetine, Ergotamine, Epinephrine, and Menadione". The Journal of Pharmacology and Experimental Therapeutics. Sep. 29, 1944. p. 292-300.

Hokuto Seo et al. "Color Sensors with Three Vertically Stacked Organic Photodetectors". Japanese Journal of Applied Physics, vol. 46, No. 49. (2007). p. L1240-L1242.

Pravat Bhattacharyya et al. "Selenocarbonyl synthesis using Woollins reagent". Tetrahedron Letters 42. Elesevier Science Ltd. (2001). p. 5949-5951.

Mikio Ihama et al. "CMOS Image Sensor with a Thin Overlaid Panchromatic Organic Photoconductive Layer for Sensors with Reduced Pixel Size". Fujifilm Corporation. (2009). p. 2123-2126.

Kazuko Takahashi et al. "Efficient Synthesis of 2-Iodo and 2-Dicyanomethyl Derivatives of Thiophene, Selenophene, Tellurophene, and Thieno[3,2-b]Thiophene". Heterocycles, vol. 43 No. 9. (1995). p. 1926-1935.

Extended European Search Report dated Mar. 24, 2017 issued in corresponding European Application No. 16200095.4.

çetin, Gülben Ardahan et al. "A new p- and n-dopable selenophene derivative and its electrochromic properties." *Organic Electronics* 10 (2009): 34-41.

Chen, Hung-Yang et al. "Comparison of thiophene- and selenophene-bridged donor-acceptor low band-gap copolymers used in bulk-heterojunction organic photovoltaics." *J. Mater. Chem.* 22 (2012): 21549-21559.

Mikhailenko, F.A. et al. "Mono- and dimethine dyes from 2-dimethylamino-5-formylfurans, -thiophenes, and -selenophenes." *Chemistry of Heterocyclic Compounds* 11.3 (1975): 273-277.

Zug, Ines and Horst Hartmann. "Preparation and Characterisation of N,N-Disubstituted 2-Amino-5H-selenophenes." *Journal of Chemical Sciences* 59 (2004): 439-442.

\* cited by examiner

COMPOUND FOR ORGANIC PHOTOELECTRIC DEVICE AND ORGANIC PHOTOELECTRIC DEVICE, IMAGE SENSOR AND ELECTRONIC DEVICE INCLUDING THE SAME

CROSS-REFERENCE TO RELATED APPLICATION

This application claims priority to and the benefit of Korean Patent Application No. 10-2015-0164996 filed in the Korean Intellectual Property Office on Nov. 24, 2015, the entire contents of which are incorporated herein by reference.

BACKGROUND

1. Field

Example embodiments relate to a compound for an organic photoelectric device, and an organic photoelectric device, an image sensor, and an electronic device including the same.

2. Description of the Related Art

A photoelectric device typically converts light into an electrical signal using photoelectric effects. The photoelectric device may include a photodiode, a phototransistor, etc., and may be applied to an image sensor, an organic light emitting diode, etc.

An image sensor including a photodiode requires typically high resolution and thus a relatively small pixel. At present, a silicon photodiode is widely used, but exhibits deteriorated sensitivity because of a smaller absorption area due to smaller pixels. Accordingly, an organic material that is capable of replacing silicon is the subject of research.

The organic material has a relatively high extinction coefficient and selectively absorbs light in a particular wavelength region depending on a molecular structure, and thus may simultaneously replace a photodiode and a color filter, thereby improving sensitivity and contributing to relatively high integration.

SUMMARY

Example embodiments provide a compound for an organic photoelectric device being capable of selectively absorbing light in a green wavelength region.

Example embodiments also provide an organic photoelectric device being capable of selectively absorbing light in a green wavelength region and improving efficiency.

Example embodiments also provide an image sensor including the organic photoelectric device.

Example embodiments also provide an electronic device including the image sensor.

According to example embodiments, a compound for an organic photoelectric device is represented by Chemical Formula 1.

[Chemical Formula 1]

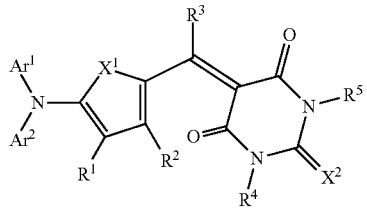

In Chemical Formula 1, $X^1$ is one of Se, Te, S(=O), S(=O)$_2$, and SiR$^a$R$^b$, wherein each of R$^a$ and R$^b$ is one of hydrogen and a $C_1$ to $C_{10}$ alkyl group, $X^2$ is one of O, S, Se, Te, and C(R$^c$)(CN), wherein R$^c$ is one of hydrogen, a cyano group (—CN), and a $C_1$ to $C_{10}$ alkyl group, each of Ar$^1$ and Ar$^2$ is independently one of a substituted or unsubstituted $C_6$ to $C_{30}$ aryl group and a substituted or unsubstituted $C_4$ to $C_{30}$ heteroaryl group, and each of R$^1$ to R$^5$ is independently one of hydrogen, deuterium, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof.

Each of the Ar$^1$ and Ar$^2$ may independently be one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

At least one of the Ar$^1$ and Ar$^2$ may be one of a substituted or unsubstituted naphthyl group, a substituted or unsubstituted anthracenyl group, a substituted or unsubstituted phenanthrenyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

The compound may have a maximum absorption wavelength ($\lambda_{max}$) of about 500 nm to about 600 nm, for example, about 525 nm to about 560 nm in a thin film state. The compound may exhibit a light absorption curve having a full width at half maximum (FWHM) of about 50 nm to about 120 nm in a thin film state.

A difference between a melting point and a deposition temperature of the compound may be greater than or equal to about 5° C., for example, greater than or equal to about 30° C. or greater than or equal to about 50° C.

According to example embodiments, an organic photoelectric device includes a first electrode and a second electrode facing each other, and an active layer between the first electrode and the second electrode and including the compound represented by Chemical Formula 1.

Each of the Ar$^1$ and Ar$^2$ may independently be one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

At least one of the $Ar^1$ and $Ar^2$ may independently be one of substituted or unsubstituted naphthyl group, a substituted or unsubstituted anthracenyl group, a substituted or unsubstituted phenanthrenyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

The active layer may have a maximum absorption peak ($\lambda_{max}$) in a wavelength region of about 500 nm to about 600 nm, for example, about 525 nm to about 560 nm. The active layer may exhibit a light absorption curve having a full width at half maximum (FWHM) of about 50 nm to about 120 nm.

A difference between a melting point and a deposition temperature of the compound may be greater than or equal to about 5° C., for example, greater than or equal to about 30° C. or greater than or equal to about 50° C.

According to example embodiments, an image sensor includes the organic photoelectric device.

The image sensor may further include a semiconductor substrate integrated with a plurality of first photo-sensing devices configured to sense light in a blue wavelength region and a plurality of second photo-sensing devices configured to sense light in a red wavelength region, and the organic photoelectric device may be on the semiconductor substrate and may be configured to selectively absorb light in a green wavelength region.

The first photo-sensing devices and the second photo-sensing devices may be stacked in a vertical direction on the semiconductor substrate.

The image sensor may further include a color filter layer between the semiconductor substrate and the organic photoelectric device, and including a blue filter configured to selectively transmit light in a blue wavelength region and a red filter configured to selectively transmit light in a red wavelength region.

The organic photoelectric device may be a green photoelectric device, and the green photoelectric device, a blue photoelectric device configured to selectively absorb light in a blue wavelength region, and a red photoelectric device configured to selectively absorb light in a red wavelength region may be stacked.

According to example embodiments, an electronic device includes the image sensor.

According to example embodiments, an active layer includes a compound for an organic photoelectric device having a melting point higher than a deposition temperature of the compound, the compound represented by the following Chemical Formula 1:

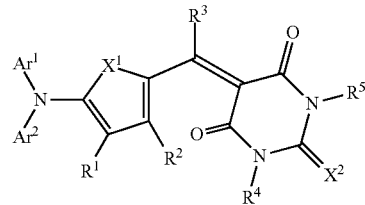

[Chemical Formula 1]

wherein, in Chemical Formula 1, $X^1$ is one of Se, Te, S(=O), S(=O)$_2$, and SiR$^a$R$^b$, wherein each of R$^a$ and R$^b$ is one of hydrogen and a C$_1$ to C$_{10}$ alkyl group, $X^2$ is one of O, S, Se, Te, and C(R$^c$)(CN), wherein R$^c$ is one of hydrogen, a cyano group (—CN), and a C$_1$ to C$_{10}$ alkyl group, each of Ar$^1$ and Ar$^2$ is independently one of a substituted or unsubstituted C$_6$ to C$_{30}$ aryl group and a substituted or unsubstituted C$_4$ to C$_{30}$ heteroaryl group, and each of R$^1$ to R$^5$ is independently one of hydrogen, deuterium, a substituted or unsubstituted C$_1$ to C$_{30}$ alkyl group, a substituted or unsubstituted C$_6$ to C$_{30}$ aryl group, a substituted or unsubstituted C$_4$ to C$_{30}$ heteroaryl group, a halogen, a cyano group (—CN), a cyano-containing group, and a combination thereof.

A difference between the melting point and the deposition temperature of the compound may be greater than or equal to about 5° C., for example, greater than or equal to about 30° C. or greater than or equal to about 50° C.

According to example embodiments, an organic photoelectric device includes a first electrode and a second electrode facing each other, and the active layer of example embodiments between the first electrode and the second electrode.

According to example embodiments an electronic device includes the organic photoelectric device of example embodiments, and may be one of a solar cell, an image sensor, a photo-detector, a photo-sensor, and an organic light emitting diode (OLED).

DETAILED DESCRIPTION

Figure 1:
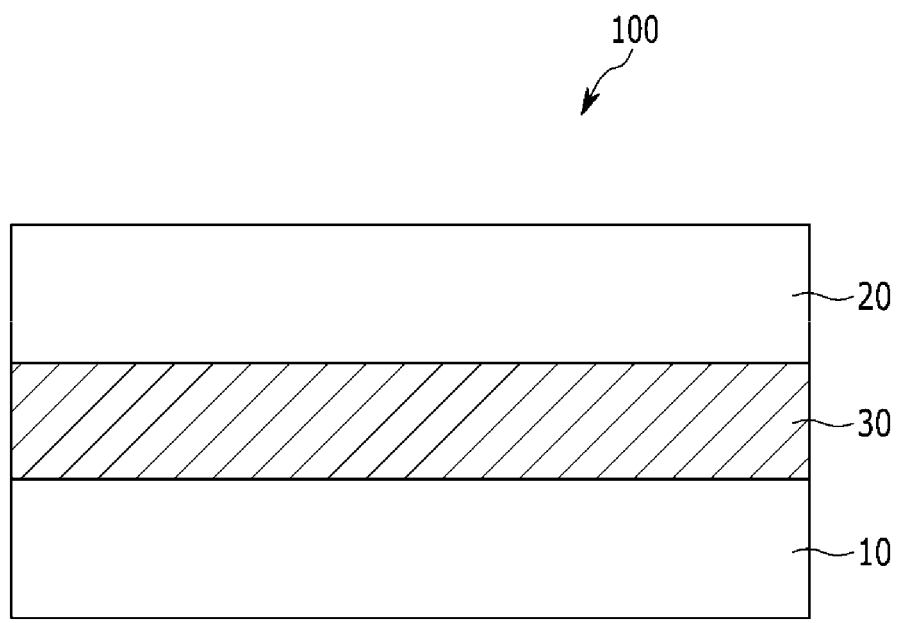
FIG. 1 is a cross-sectional view showing an organic photoelectric device according to example embodiments.

Example embodiments will hereinafter be described in detail, and may be more easily performed by those who have common knowledge in the related art. However, this disclosure may be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

As used herein, when specific definition is not otherwise provided, the term "substituted" refers to one substituted with a substituent selected from a halogen (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid or a salt thereof, a $C_1$ to $C_{20}$ alkyl group, a $C_1$ to $C_{20}$ alkoxy group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ heteroalkyl group, a $C_1$ to $C_{20}$ heteroaryl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof.

As used herein, when specific definition is not otherwise provided, the term "hetero" refers to one including 1 to 3 heteroatoms selected from N, O, S, P, and Si.

As used herein, the term "alkyl group" for example refers to a methyl group, an ethyl group, a propyl group, an isopropyl group, a n-butyl group, an isobutyl group, a t-butyl group, a pentyl group, a hexyl group, a cyclopropyl group, a cyclobutyl group, a cyclopentyl group, a cyclohexyl group, etc.

As used herein, the term "aryl group" refers to a cyclic substituent where all elements have p-orbitals, and these p-orbitals forms conjugation, and includes a monocyclic, non-fused polycyclic or fused ring polycyclic (i.e., rings sharing adjacent pairs of carbon atoms) functional group.

As used herein, when specific definition is not otherwise provided, the term "cyano-containing group" refers to a $C_1$ to $C_{30}$ alkyl group, a $C_2$ to $C_{30}$ alkenyl group, or a $C_2$ to $C_{30}$ alkynyl group where at least one hydrogen is replaced by a cyano group. Specific examples of a cyano-containing group may be a dicyanomethyl group, a dicyanovinyl group, and a cyanoethynyl group.

As used herein, when a definition is not otherwise provided, the term "combination thereof" refers to at least two substituents bound to each other by a single bond or a $C_1$ to $C_{10}$ alkylene group, or at least two fused substituents.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," etc.) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hereinafter, a compound for an organic photoelectric device according to example embodiments is described.

A compound for an organic photoelectric device according to example embodiments is represented by Chemical Formula 1.

[Chemical Formula 1]

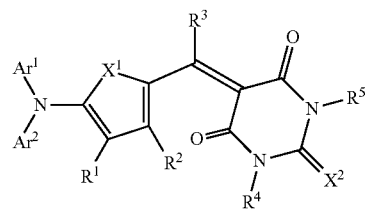

In Chemical Formula 1, $X^1$ is one of Se, Te, S(=O), S(=O)$_2$, and SiR$^a$R$^b$, wherein each of R$^a$ and R$^b$ is one of hydrogen and a C$_1$ to C$_{10}$ alkyl group, $X^2$ is one of O, S, Se, Te, and C(R$^c$)(CN), wherein R$^c$ is one of hydrogen, a cyano group (—CN), and a C$_1$ to C$_{10}$ alkyl group, each of Ar$^1$ and Ar$^2$ is independently one of a substituted or unsubstituted C$_6$ to C$_{30}$ aryl group and a substituted or unsubstituted C$_4$ to C$_{30}$ heteroaryl group, and each of R$^1$ to R$^5$ is independently one of hydrogen, deuterium, a substituted or unsubstituted C$_1$ to C$_{30}$ alkyl group, a substituted or unsubstituted C$_6$ to C$_{30}$ aryl group, a substituted or unsubstituted C$_4$ to C$_{30}$ heteroaryl group, a halogen, a cyano group (—CN), a cyano-containing group, and a combination thereof.

In example embodiments, each of R$^4$ and R$^5$ may independently be hydrogen. In this case, heat resistance of the compound for an organic photoelectric device may be improved.

In example embodiments, Ar$^1$ and Ar$^2$ and R$^1$ to R$^5$ of Chemical Formula 1 may be substituted with a halogen (i.e., —F, —Cl, —Br or —I), a cyano group (—CN), a C$_1$ to C$_6$ alkyl group or a C$_1$ to C$_6$ alkoxy group. In example embodiments, the halogen may be a chloro group (—Cl) or a fluoro group (—F).

The compound for an organic photoelectric device includes an electron donor moiety and an electron acceptor moiety within one molecule and thus has bipolar characteristics.

In Chemical Formula 1, Ar$^1$ and Ar$^2$ may be a single or fused aromatic ring of a substituted or unsubstituted C$_6$ to C$_{30}$ aryl group or a substituted or unsubstituted C$_4$ to C$_{30}$ heteroaryl group, for example, a single or fused aromatic ring of a substituted or unsubstituted C$_6$ to C$_{20}$ or C$_8$ to C$_{20}$ aryl group or a substituted or unsubstituted C$_4$ to C$_{20}$ heteroaryl group. By contrast, an aromatic group having aromatic rings connected through a single bond or another linking group has a broken conjugation structure, and thus, may not provide a desirable conjugation length.

Each of the Ar$^1$ and Ar$^2$ may be independently one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

In example embodiments, the substituted phenyl group, substituted naphthyl group, substituted anthracenyl group, substituted phenanthrenyl group, substituted pyridinyl group, substituted pyridazinyl group, substituted pyrimidinyl group, substituted pyrazinyl group, substituted quinolinyl group, substituted isoquinolinyl group, substituted naphthyridinyl group, substituted cinnolinyl group, substituted quinazolinyl group, substituted phthalazinyl group, substituted benzotriazinyl group, substituted pyridopyrazinyl group, substituted pyridopyrimidinyl group and substituted pyridopyridazinyl group may independently substituted with a cyano group or a halogen. Herein, because heat resistance characteristics of the compound for an organic photoelectric device are improved, the compound may be desirably applied in a subsequent heat treatment process during manufacture of a device.

At least one of the Ar$^1$ and Ar$^2$ may be one of a substituted or unsubstituted naphthyl group, a substituted or unsubstituted anthracenyl group, a substituted or unsubstituted phenanthrenyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group. In this way, when at least one of the Ar$^1$ and Ar$^2$ is a substituent having at least two fused aromatic rings, the substituent may decrease an intermolecular interaction among molecules, and thus, suppress aggregation of the molecules in a film state. Herein, absorption selectivity of a green wavelength may be improved.

When the Ar$^1$ and Ar$^2$ are an alkyl group or are linked to each other to provide an N-containing aliphatic cyclic group, instead of the aromatic group, the compound structure has planarity, and thus, a full width at half maximum (FWHM) of a light absorption curve may become undesirably wide.

In addition, the absorption coefficient of the compound for an organic photoelectric device may be increased, and thus, efficiency of the device may be improved.

The compound for an organic photoelectric device may have a maximum absorption wavelength ($\lambda_{max}$) in wavelength ranges of about 500 nm to about 600 nm, for example, about 525 nm to about 560 nm, about 528 nm to about 560 nm or about 528 nm to about 550 nm in a thin film state.

The compound for an organic photoelectric device may show a light absorption curve having a full width at half maximum (FWHM) of about 50 nm to about 120 nm in a thin film state. Herein, the FWHM is a difference between two wavelengths corresponding to half of a hetight of a maximum absorption point. As used herein, when a specific definition is not otherwise provided, the FWHM may be defined by absorbance measured by UV-Vis spectroscopy. When the full width at half maximum (FWHM) is within the range, selectivity in a green wavelength region may be increased. The thin film may be a thin film deposited under a vacuum condition.

The deposition process may provide a uniform thin film without impurities, but when the compound has a lower melting point than a deposition temperature, decomposed products of the compound may be deposited together, which deteriorates performance of the device. Accordingly, it is desirable for the melting point of a compound to be higher than the deposition temperature.

A difference between the melting point and the deposition temperature of the compound for an organic photoelectric device may be greater than or equal to about 5° C., for example, greater than or equal to about 30° C. or greater than or equal to about 50° C. Accordingly, the compound for an organic photoelectric device has a higher melting point than the deposition temperature, and thus, is not decomposed at a lower temperature than the deposition temperature and may be used in a deposition process. When the compound has a melting point within the range, a film may be stably deposited, and decomposed products of the compound may be reduced, thereby providing an organic photoelectric device having improved photoelectric conversion performance. In addition, because properties of the film are not deteriorated during a production process, both reliability and mass productivity may be improved.

The compound for an organic photoelectric device may be a p type semiconductor compound. Because the compound for an organic photoelectric device works as a p-type semiconductor, the compound may be appropriately used, as long as it has a higher LUMO level than an n-type semiconductor compound. For example, when the compound is mixed with an n-type semiconductor compound, e.g., fullerene, the compound desirably has a higher LUMO level than the fullerene having a LUMO level of 4.2 eV. As for the appropriate HOMO-LUMO level of the compound, when the compound for an organic photoelectric device has a HOMO level ranging from about 5.0 eV to about 5.8 eV and an energy bandgap ranging from about 1.9 eV to about 2.3 eV, the LUMO level of the compound is in a range of about 2.7 eV to about 3.9 eV. The compound for an organic photoelectric device having a HOMO level, an LUMO level and an energy bandgap within the ranges may be used as a p-type semiconductor compound effectively absorbing light in a green wavelength region, and thus, has relatively high external quantum efficiency (EQE) and resultantly improves photoelectric conversion efficiency.

The compound for an organic photoelectric device may have a molecular weight of about 300 to about 1500, for example, about 350 to about 1200, or about 400 to about 900. When the compound has a molecular weight within the range, the crystallinity of the compound and thermal decomposition during formation of a thin film by deposition may be inhibited.

The compound for an organic photoelectric device of Chemical Formula 1 may be a compound represented by Chemical Formula 2.

[Chemical Formula 2]

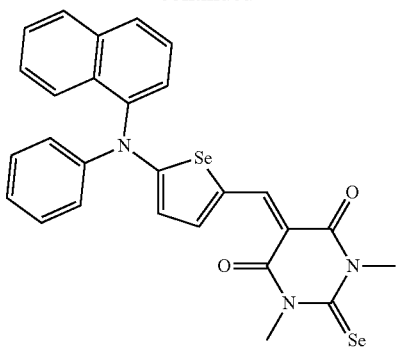

-continued

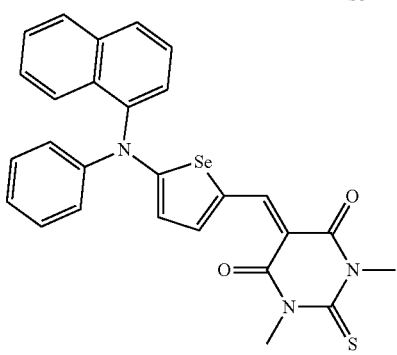

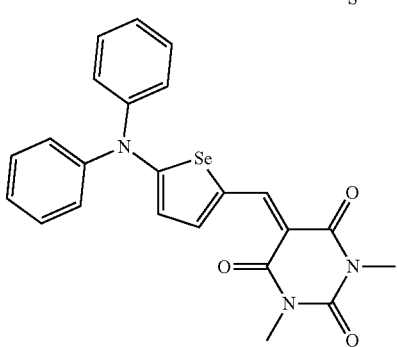

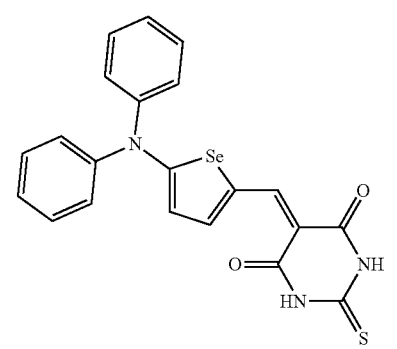

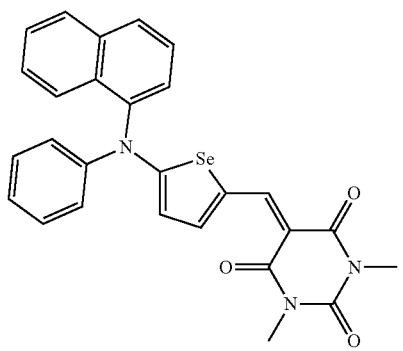

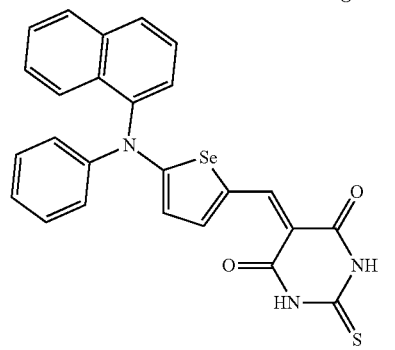

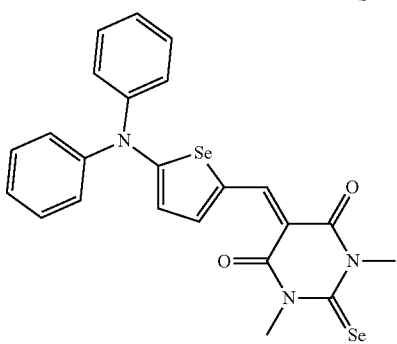

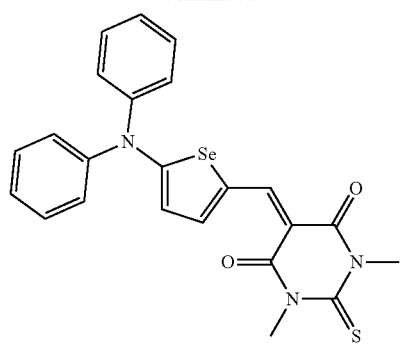
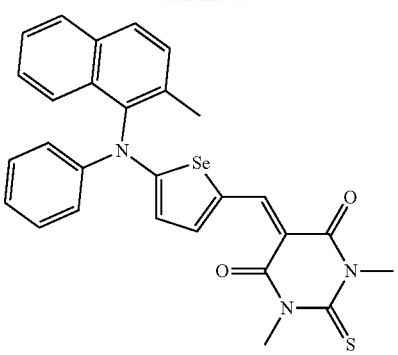

-continued
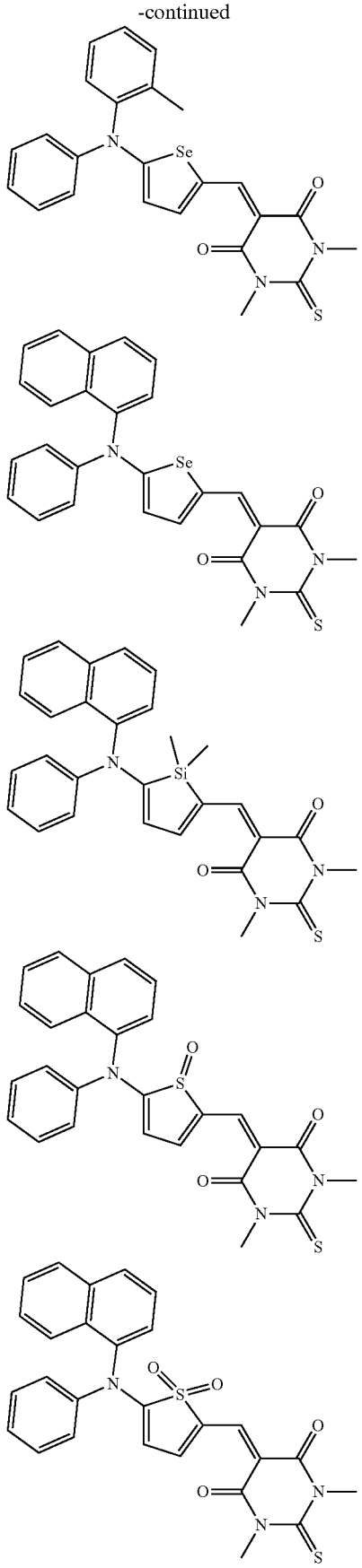
-continued
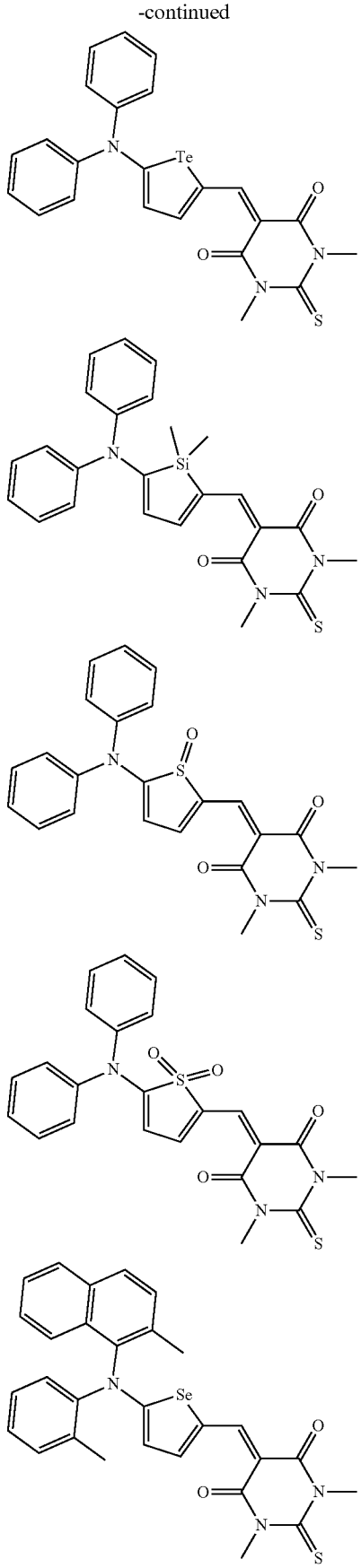

-continued
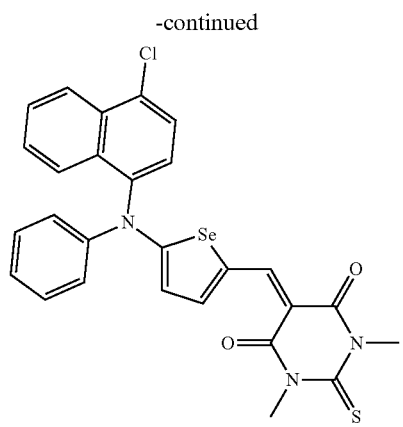
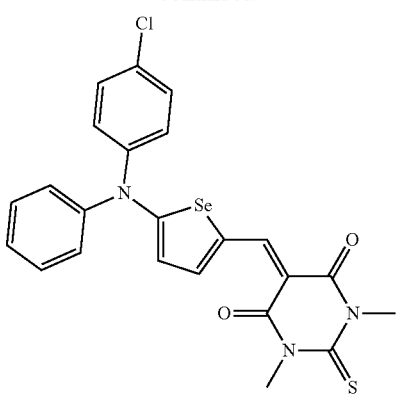
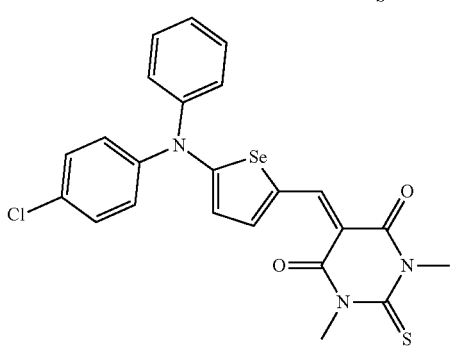
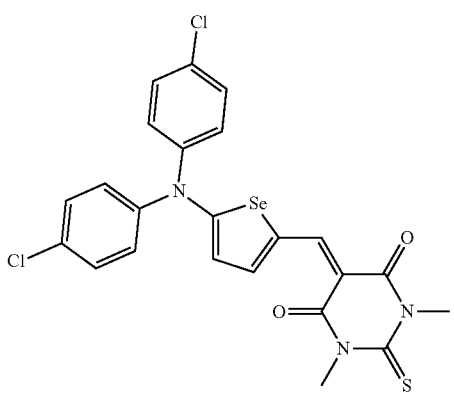
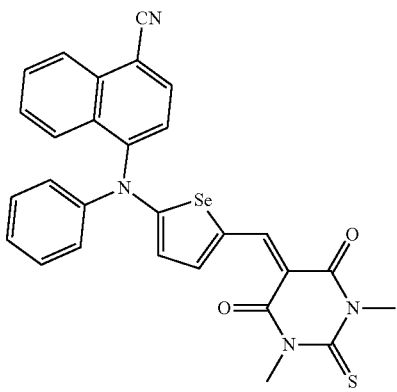

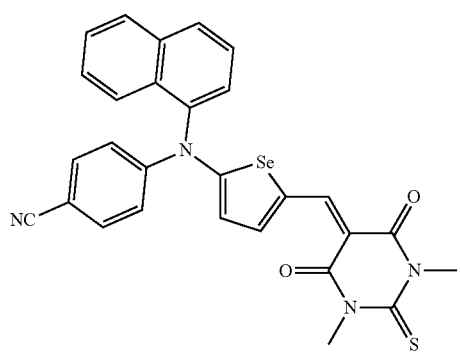
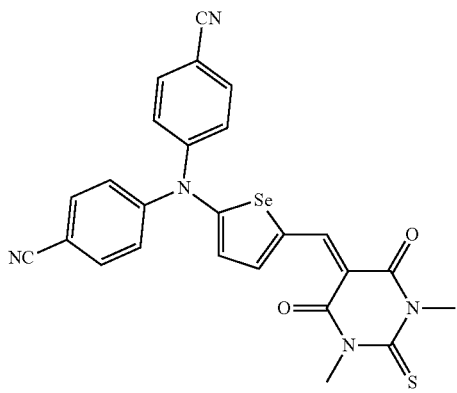
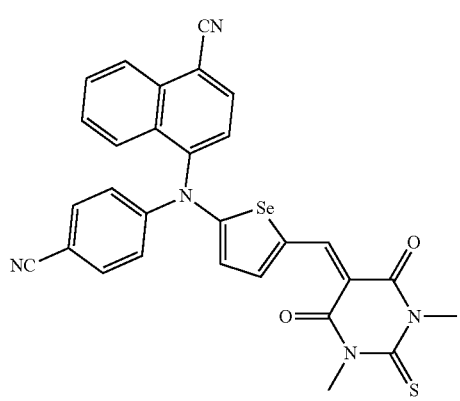
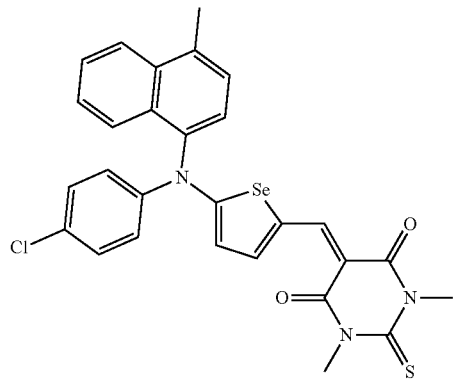
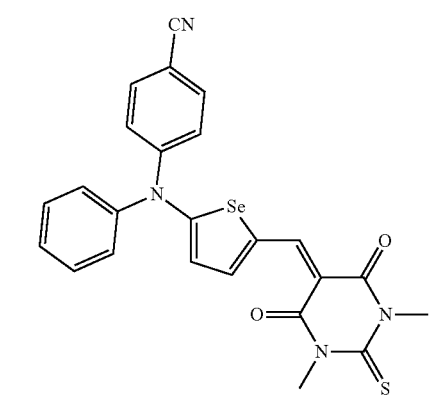
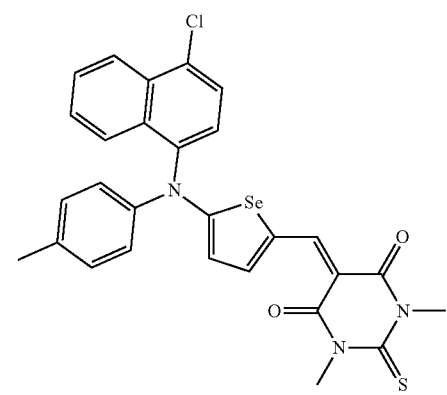
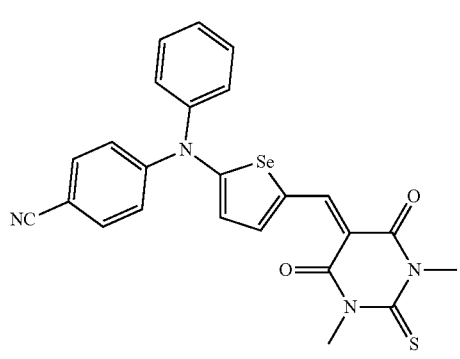
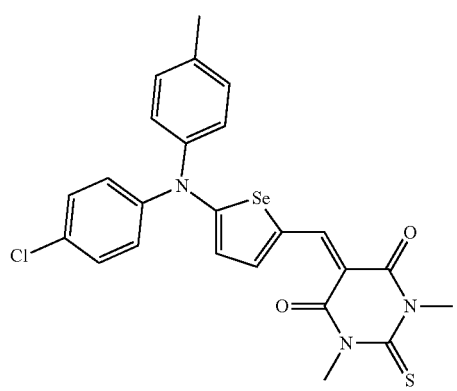

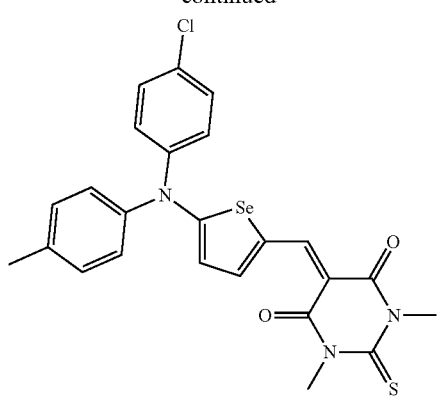
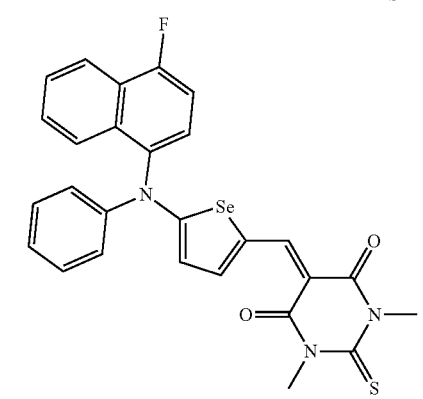
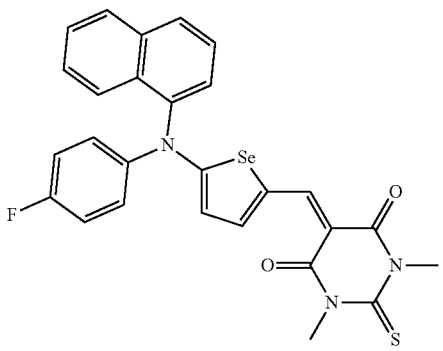
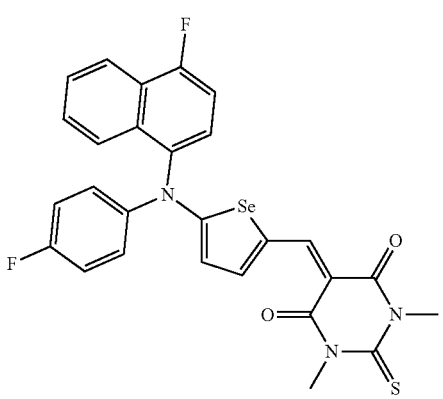
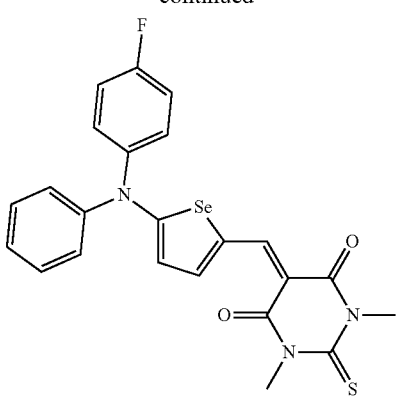
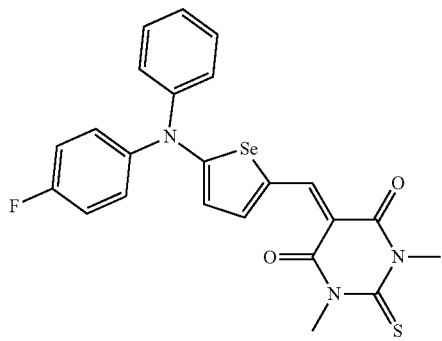
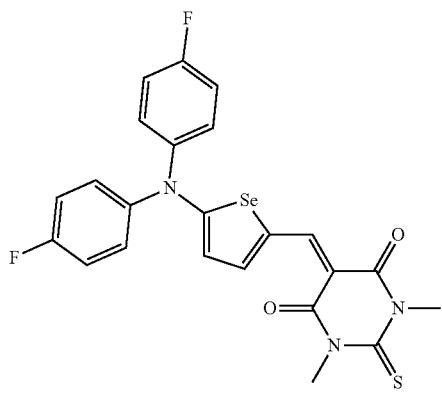
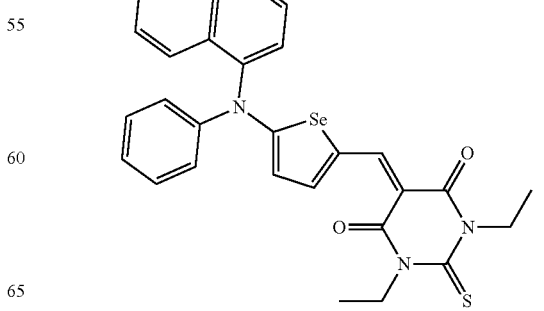

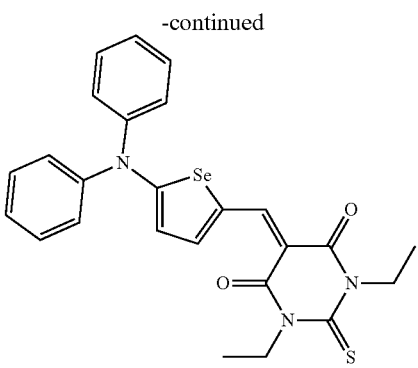

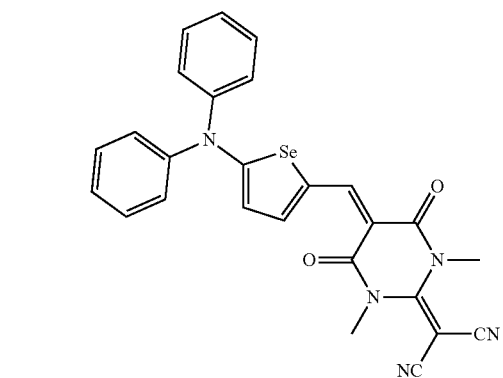

The compound for an organic photoelectric device is a compound that selectively absorbs light in a green wavelength region, and may have a maximum absorption wavelength ($\lambda_{max}$) at about 525 nm to about 560 nm, about 528 nm to about 560 nm or about 528 nm to about 550 nm.

Hereinafter, an organic photoelectric device including the compound according to example embodiments is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor (e.g., indium tin oxide (ITO) or indium zinc oxide (IZO)), or a metal thin layer of a thin monolayer or multilayer. When one of the first electrode 10 and the second electrode 20 is a non-light-transmitting electrode, the first electrode 10 or the second electrode 20 may be made of, for example, an opaque conductor (e.g., aluminum (Al)).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound for an organic photoelectric device may act as a p-type semiconductor compound in the active layer 30.

The compound for an organic photoelectric device is a compound that selectively absorbs light in a green wavelength region, and the active layer 30 including the compound may have a maximum absorption wavelength ($\lambda_{max}$) at about 500 nm to about 600 nm, for example, about 525 nm to about 560 nm, about 528 nm to about 560 nm or about 528 nm to about 550 nm.

The active layer 30 may show a light absorption curve having a relatively narrow full width at half maximum (FWHM) of about 50 nm to about 120 nm. Accordingly, the active layer 30 has higher selectivity for light in a green wavelength region.

The active layer 30 may further include an n-type semiconductor compound for forming a pn junction.

The n-type semiconductor compound may be subphthalocyanine or a subphthalocyanine derivative, fullerene or a fullerene derivative, thiophene or a thiophene derivative, or a combination thereof.

The fullerene may include C50, C60, C70, C76, C78, C80, C82, C84, C90, C96, C240, C540, a mixture thereof, a fullerene nanotube, etc. The "fullerene derivatives" may refer to compounds of these fullerenes having a substituent attached thereto. The fullerene derivatives may include substituents such as alkyl groups, aryl groups, or heterocyclic groups. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathiin ring, a phenothiazine ring, or a phenazine ring.

The subphthalocyanine or subphthalocyanine derivative may be represented by Chemical Formula 3.

[Chemical Formula 3]

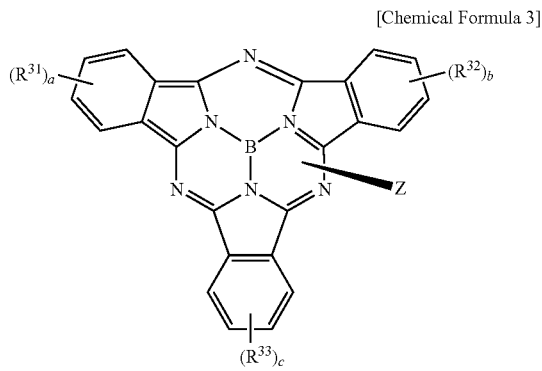

[Chemical Formula 6]

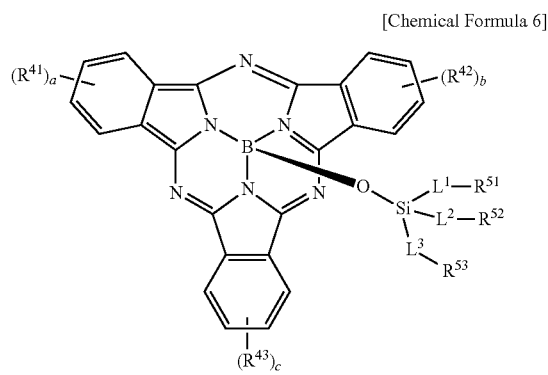

In Chemical Formula 3, each of $R^{31}$ to $R^{33}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, a, b and c are integers ranging from 1 to 3, and Z is a halogen, for example, F or Cl.

The halogen may refer to F, Cl, Br, or I, and the halogen-containing group may refer to an alkyl group where at least one of hydrogen is replaced by F, Cl, Br, or I.

The thiophene derivative may be, for example represented by Chemical Formula 4 or Chemical Formula 5, but is not limited thereto.

[Chemical Formula 4]

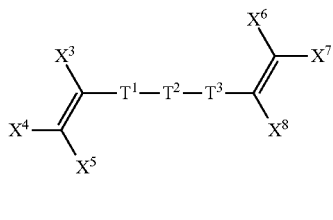

[Chemical Formula 5]

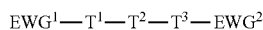

$EWG^1-T^1-T^2-T^3-EWG^2$

In Chemical Formulae 4 and 5, $T^1$, $T^2$, and $T^3$ are aromatic rings including substituted or unsubstituted thiophene moieties, $T^1$, $T^2$, and $T^3$ are each independently present or are fused to each other, each of $X^3$ to $X^8$ is independently one of hydrogen, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, a cyano group, and a combination thereof, and each of $EWG^1$ and $EWG^2$ is independently electron withdrawing groups.

For example, in the Chemical Formula 4, at least one of $X^3$ to $X^8$ is an electron withdrawing group, for example a cyano group or a cyano-containing group.

The active layer 30 may further include a second p-type semiconductor compound selectively absorbing green light. The p-type semiconductor compound may be a compound represented by Chemical Formula 6.

In Chemical Formula 6, each of $R^{41}$ to $R^{43}$ are independently one of a hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_2$ to $C_{30}$ aliphatic heterocyclic group, a substituted or unsubstituted $C_2$ to $C_{30}$ aromatic heterocyclic group, a substituted or unsubstituted $C_1$ to $C_{30}$ alkoxy group, a substituted or unsubstituted $C_6$ to $C_{30}$ aryloxy group, thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group (e.g., a substituted or unsubstituted $C_0$ to $C_{30}$ aminosulfonyl group, a substituted or unsubstituted $C_1$ to $C_{30}$ alkylsulfonyl group or a substituted or unsubstituted arylsulfonyl group), and a combination thereof, or $R^{41}$ to $R^{43}$ are independently present or are fused to each other to provide a ring, each of $L^1$ to $L^3$ is independently one of a single bond, a substituted or unsubstituted $C_1$ to $C_{30}$ alkylene group, a substituted or unsubstituted $C_6$ to $C_{30}$ arylene group, a divalent substituted or unsubstituted $C_2$ to $C_{30}$ heterocyclic group, or a combination thereof, each of $R^{51}$ to $R^{53}$ is independently one of a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, a substituted or unsubstituted $C_1$ to $C_{30}$ alkoxy group, a substituted or unsubstituted amine group (e.g., a substituted or unsubstituted $C_1$ to $C_{30}$ alkylamine group or a substituted or unsubstituted $C_6$ to $C_{30}$ arylamine group), a substituted or unsubstituted silyl group, and a combination thereof, and a to c are each independently an integer ranging from 0 to 4.

The second p-type semiconductor compound selectively absorbing green light may be included in an amount of about 50 to about 300 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, etc.

The intrinsic layer (I layer) may include the compound of Chemical Formula 1 and the n-type semiconductor compound in a volume ratio of about 1:100 to about 100:1. The compound of Chemical Formula 1 and the n-type semiconductor compound may be included in a volume ratio ranging from about 1:50 to about 50:1 within the range, for example, about 1:10 to about 10:1, or about 1:1. When the compound of Chemical Formula 1 and the n-type semiconductor compound have a composition ratio within the range, an exciton may be effectively produced and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm, for example, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90% or more.

In the organic photoelectric device 100, when light enters from the first electrode 10 and/or second electrode 20, and when the active layer 30 absorbs light having a given or predetermined wavelength, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
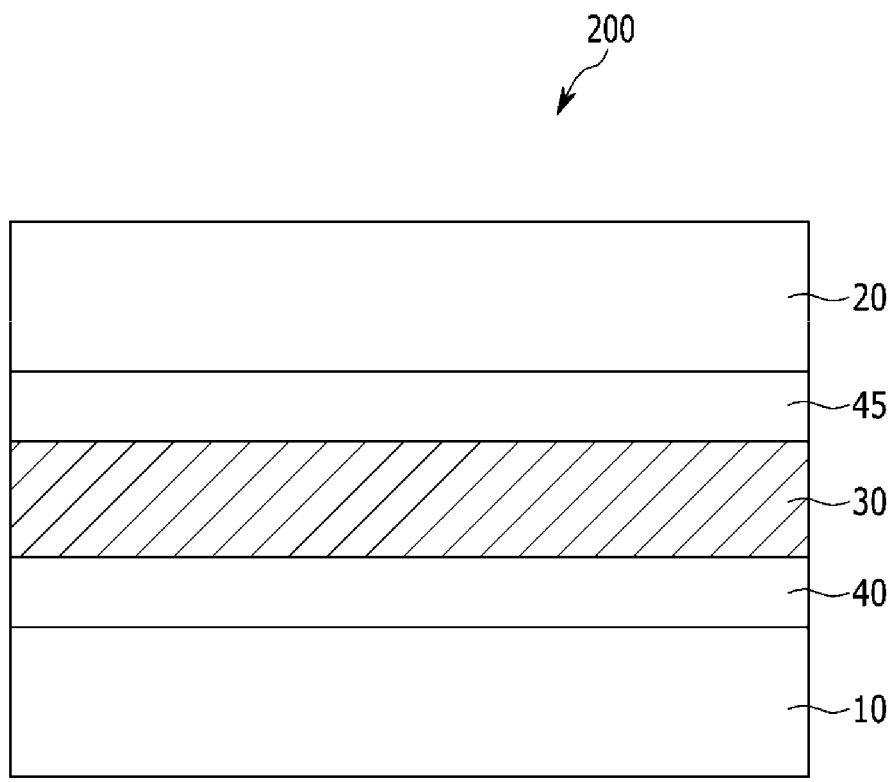
FIG. 2 is a cross-sectional view showing an organic photoelectric device according to example embodiments.

FIG. 2 is a cross-sectional view showing an organic photoelectric device according to example embodiments.

Referring to FIG. 2, an organic photoelectric device 200 according to the present embodiment includes a first electrode 10 and a second electrode 20 facing each other, and an active layer 30 between the first electrode 10 and the second electrode 20, like the example embodiment illustrated in FIG. 1.

However, the organic photoelectric device 200 according to the present embodiment further includes charge auxiliary layers 40 and 45 between the first electrode 10 and the active layer 30, and the second electrode 20 and the active layer 30, unlike the example embodiment illustrated in FIG. 1. The charge auxiliary layers 40 and 45 may be configured to facilitate the transfer of holes and electrons separated from the active layer 30, so as to increase efficiency.

The charge auxiliary layers 40 and 45 may be at least one selected from a hole injection layer (HIL) configured to facilitate hole injection, a hole transport layer (HTL) configured to facilitate hole transport, an electron blocking layer (EBL) inhibiting or preventing electron transport, an electron injection layer (EIL) configured to facilitate electron injection, an electron transport layer (ETL) configured to facilitate electron transport, and a hole blocking layer (HBL) inhibiting or preventing hole transport.

The charge auxiliary layers 40 and 45 may include, for example, an organic material, an inorganic material, or an organic/inorganic material. The organic material may be an organic compound having hole or electron injection and/or transportation characteristics, and the inorganic material may be, for example, a metal oxide (e.g., molybdenum oxide, tungsten oxide, nickel oxide, etc).

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one of, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example, a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
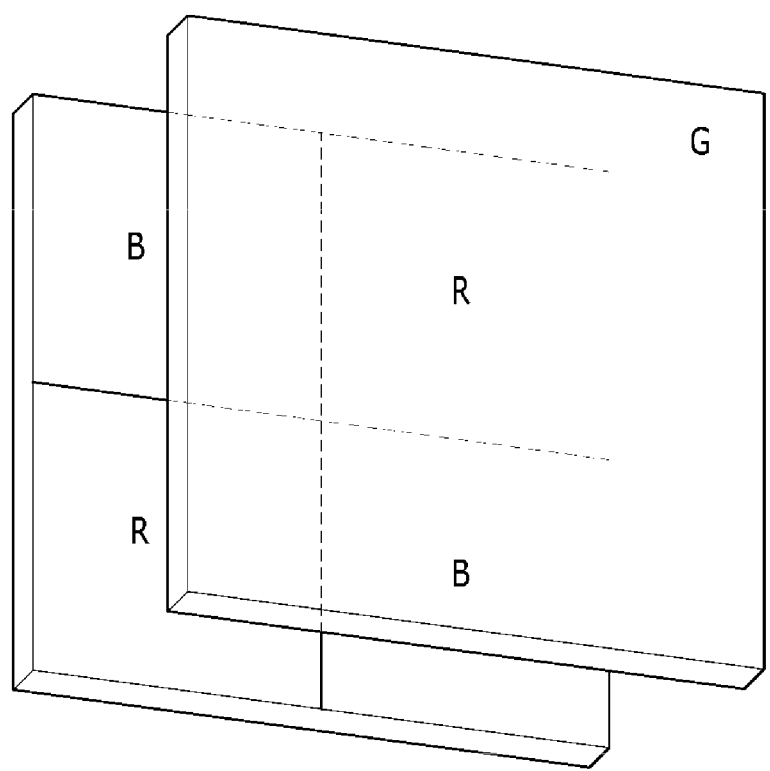
FIG. 3 is a schematic view showing an organic CMOS image sensor according to example embodiments.
Figure 4:
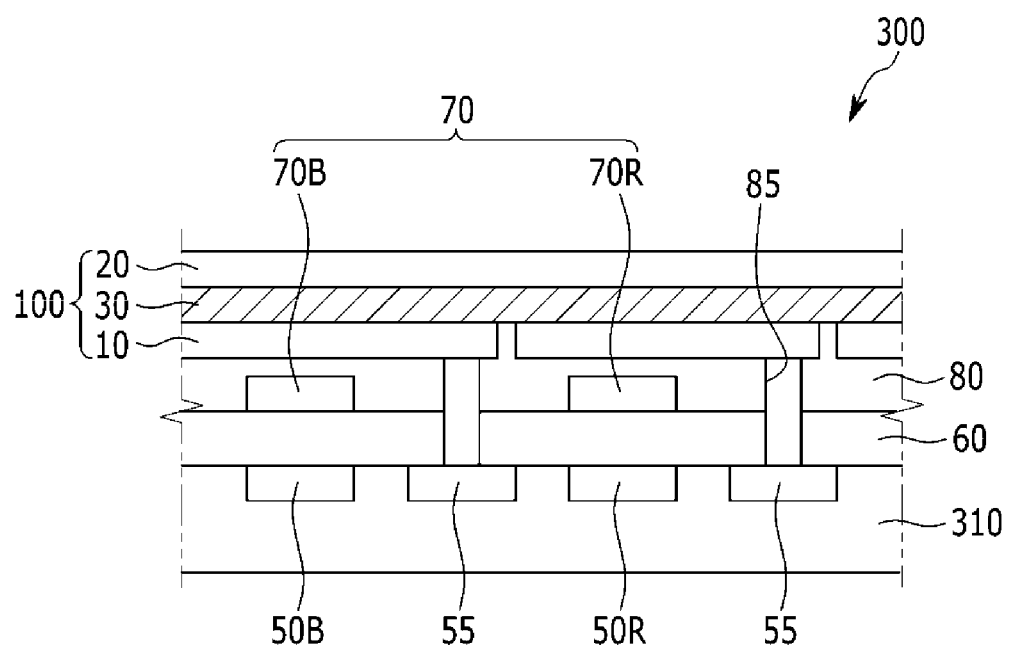
FIG. 4 is a cross-sectional view showing the organic CMOS image sensor of FIG. 3.

FIG. 3 is a schematic top plan view showing an organic CMOS image sensor according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage device 55, a lower insulation layer 60, a color filter layer 70, an upper insulation layer 80, and an organic photoelectric device 100.

The semiconductor substrate 310 may be a silicon substrate, and is integrated with the photo-sensing device 50, the transmission transistor (not shown), and the charge storage device 55. The photo-sensing devices 50R and 50B may be photodiodes.

The photo-sensing devices 50B and 50R, the transmission transistor, and/or the charge storage device 55 may be integrated in each pixel, and as shown in the drawing, the photo-sensing devices 50B and 50R may be respectively included in a blue pixel and a red pixel and the charge storage device 55 may be included in a green pixel.

The photo-sensing devices 50B and 50R sense light, the information sensed by the photo-sensing devices may be transferred by the transmission transistor, the charge storage device 55 is electrically connected with the organic photoelectric device 100, and the information of the charge storage device 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having relatively low resistivity, for example, aluminum (Al), copper (Cu), silver (Ag), and alloys thereof, but are not limited thereto. Further, example embodiments are not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material, e.g., a silicon oxide and/or a silicon nitride, or a low dielectric constant (low K) material, e.g., SiC, SiCOH, SiCO, and SiOF. The lower insulation layer 60 has a trench exposing the charge storage device 55. The trench may be filled with fillers.

A color filter layer 70 is formed on the lower insulation layer 60. The color filter layer 70 includes a blue filter 70B formed in the blue pixel and configured to selectively transmit blue light and a red filter 70R formed in the red pixel and configured to selectively transmit red light. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage device 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through the first electrode 10 and may be sensed in the photo-sensing devices 50B and 50R.

As described above, the organic photoelectric devices configured to selectively absorb light in a green wavelength region are stacked and thereby a size of an image sensor may be decreased and a down-sized image sensor may be realized.

As described above, the compound represented by the Chemical Formula 1 may be used as a p-type or n-type semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In FIG. 4, the organic photoelectric device 100 of FIG. 1 is included, but example embodiments are not limited thereto. Thus, the organic photoelectric device 200 of FIG. 2 may be applied in the same manner.

Figure 5:
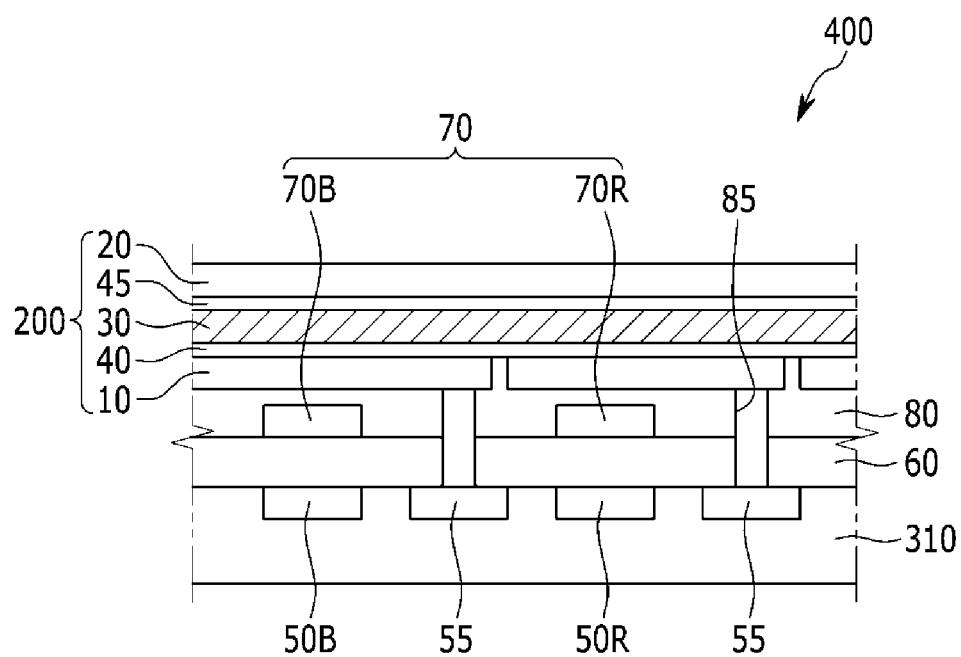
FIG. 5 is a schematic cross-sectional view showing an organic CMOS image sensor according to example embodiments.

FIG. 5 shows a structure of an image sensor having such a structure, and is a cross-sectional view of an organic CMOS image sensor 400 including the organic photoelectric device 200 in FIG. 2.

Figure 6:
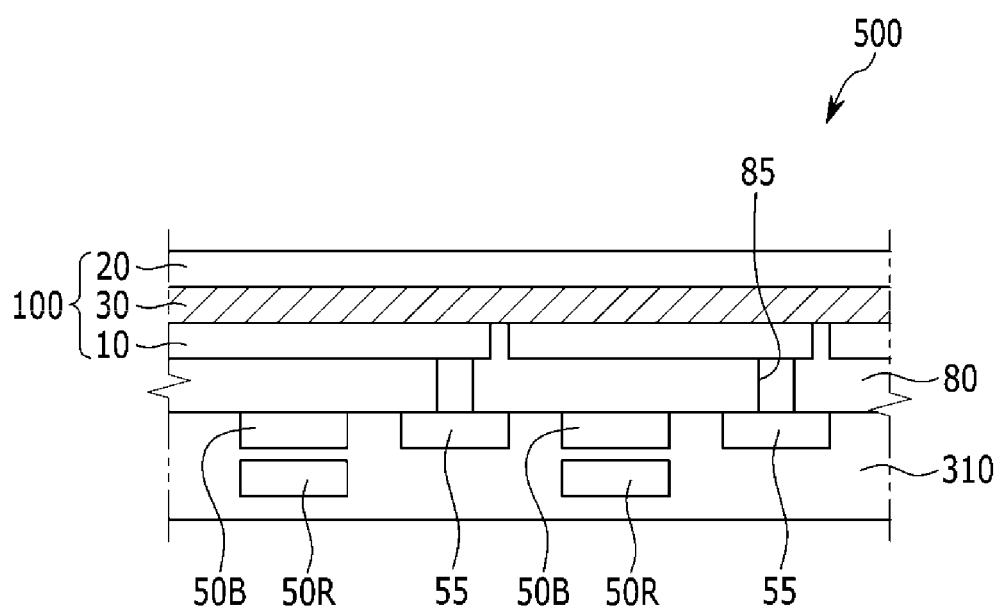
FIG. 6 is a schematic cross-sectional view showing an organic CMOS image sensor according to example embodiments.

FIG. 6 is a cross-sectional view showing the organic CMOS image sensor according to example embodiments.

Referring to FIG. 6, the organic CMOS image sensor 500 according to the present embodiment includes a semiconductor substrate 310 integrated with photo-sensing devices 50B and 50R, a transmission transistor (not shown), a charge storage device 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage device 55, and the information of the charge storage device 55 may be transferred by the transmission transistor (not shown). The blue photo-sensing device 50B and the red photo-sensing device 50R may selectively absorb light in each wavelength region depending on a stack depth.

As described above, the organic photoelectric devices configured to selectively absorb light in a green wavelength region are stacked and the red photo-sensing device and the blue photo-sensing device are stacked, and thereby, a size of an image sensor may be decreased and a down-sized image sensor may be realized. As described above, the organic photoelectric device 100 has improved green wavelength selectivity, and crosstalk caused by unnecessary absorption of light in a wavelength region except green wavelength region may be decreased while increasing sensitivity.

In FIG. 6, the organic photoelectric device 100 of FIG. 1 is included, but example embodiments are not limited thereto. Thus, the organic photoelectric device 200 of FIG. 2 may be applied in the same manner.

Figure 7:
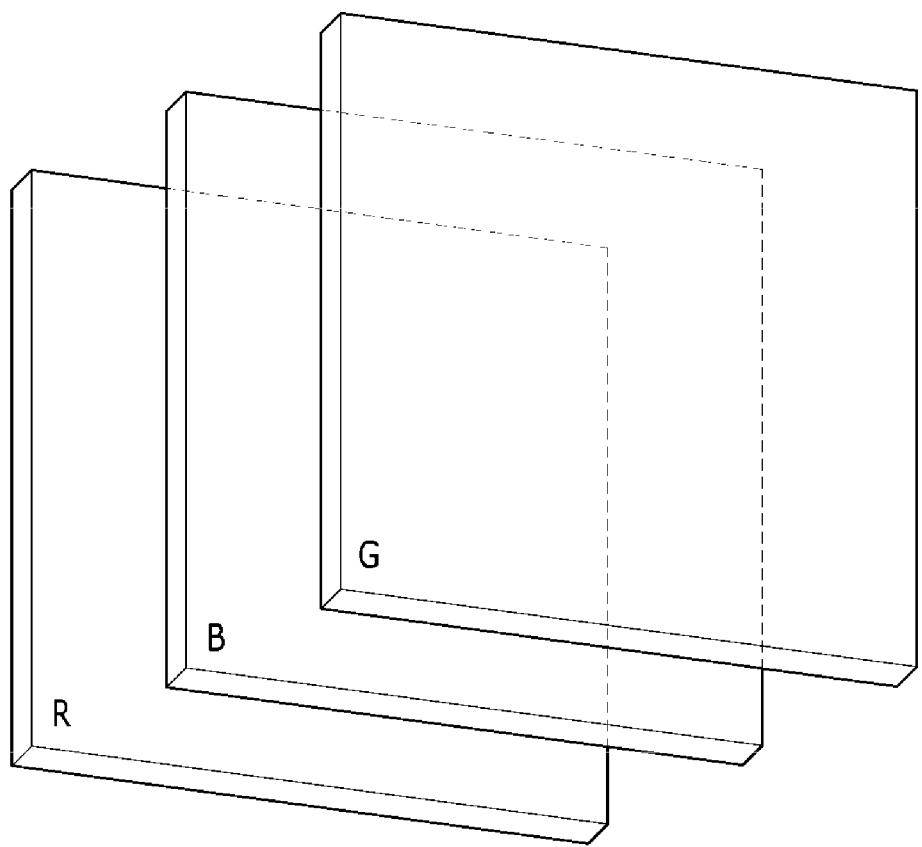
FIG. 7 is a schematic view showing an organic CMOS image sensor according to example embodiments.

FIG. 7 is a schematic view showing an organic CMOS image sensor according to example embodiments.

Referring to FIG. 7, the organic CMOS image sensor according to the present embodiment includes a green photoelectric device (G) configured to selectively absorb light in a green wavelength region, a blue photoelectric device (B) configured to selectively absorb light in a blue wavelength region, and a red photoelectric device (R) configured to selectively absorb light in a red wavelength region that are stacked.

In the drawing, the red photoelectric device (R), the blue photoelectric device (B), and the green photoelectric device (G) are sequentially stacked, but the stack order may be changed without limitation.

The green photoelectric device may be the above organic photoelectric device 100, the blue photoelectric device may include electrodes facing each other and an active layer interposed therebetween and including an organic material configured to selectively absorb light in a blue wavelength region, and the red photoelectric device may include electrodes facing each other and an active layer interposed therebetween and including an organic material configured to selectively absorb light in a red wavelength region.

As described above, the organic photoelectric device configured to selectively absorb light in a green wavelength region, the organic photoelectric device configured to selectively absorb light in a red wavelength region, and the organic photoelectric device configured to selectively absorb light in a blue wavelength region are stacked, and thereby a size of an image sensor may be decreased and a down-sized image sensor may be realized.

The image sensor may be applied to various electronic devices, for example, a mobile phone and/or a digital camera, but is not limited thereto.

Hereinafter, the present disclosure is illustrated in more detail with reference to examples. However, these are examples, and the present disclosure is not limited thereto.

Synthesis Example 1: Synthesis of the Compound Represented by Chemical Formula 1-1 (1,3-dimethyl-5-((5-(naphthalen-1-yl(phenyl)amino)selenophen-2-yl)methylene)-2-thioxodihydropyrimidine-4,6(1H,5H)-dione)

[Chemical Formula 1-1]

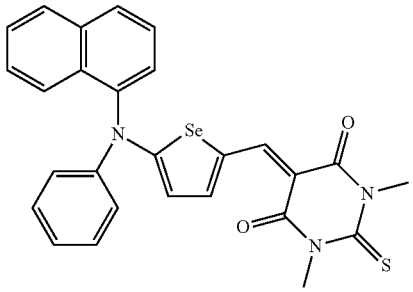

[Reaction Scheme 1-1]

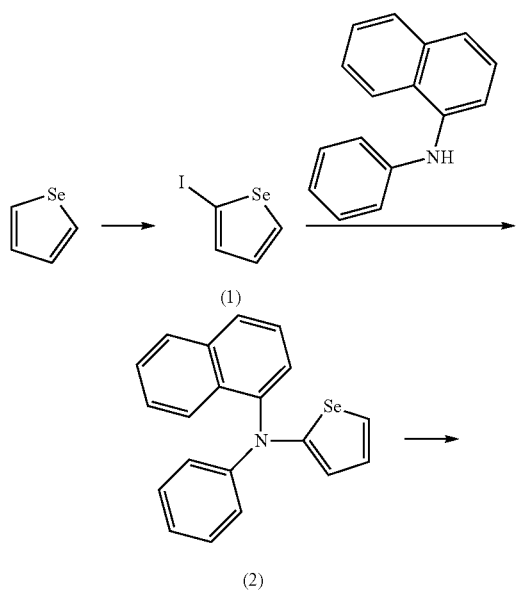

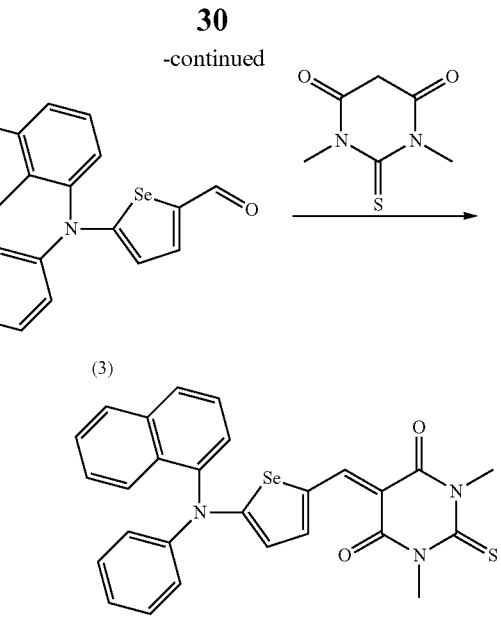

(i) Synthesis of Compound (1)

2-iodoselenophene is synthesized according to method disclosed in Efficient Synthesis of 2-Iodo and 2-dicyanomethyl Derivatives of Thiophene, Selenophene, Tellurophene, and Thieno[3,2-b]thiophene (Takahashi, K.; Tarutani, S. Heterocycles 1996, 43, 1927-1935).

(ii) Synthesis of Compound (2)

1 g (3.89 mmol) of 2-iodoselenophene and 0.77 g (3.54 mmol) of 1-naphthylphenylamine is heated and refluxed in 6 ml of anhydrous toluene in the presence of 0.1 g (0.18 mmol) of Pd(dba)$_2$, 0.036 g (0.18 mmol) of P(tBu)$_3$, and 0.37 g (3.89 mmol) of NaOtBu for 2 hours. A product therefrom is separated and purified through silica gel column chromatography (toluene:hexane=1:4 volume ratio), obtaining 0.55 g of N-(naphthalen-1-yl)-N-phenylselenophen-2-amine (a yield of 44%).

(iii) Synthesis of Compound (3)

0.16 ml of phosphoryl chloride is added to 0.5 ml of N,N-dimethylformamide in a dropwise fashion at −15° C., and the mixture stirred at room temperature (24° C.) for 2 hours. The resultant is slowly added in a dropwise fashion to a mixture of 10 ml of dichloromethane, and 0.4 g of the compound 2 at −15° C., and the obtained mixture is stirred at room temperature for 30 minutes and concentrated under a reduced pressure. Subsequently, 5 ml of water is added thereto, a sodium hydroxide aqueous solution is added thereto until pH 14, and the mixture is stirred at room temperature (24° C.) for 2 hours. Then, an organic layer extracted therefrom with ethyl acetate is washed with a sodium chloride aqueous solution and dried by adding anhydrous magnesium sulfate thereto. A product obtained therefrom is separated and purified through silica gel column chromatography (hexane:dichloromethane=3:2 volume ratio), obtaining 0.24 g of 5-(naphthalen-1-yl(phenyl)amino)selenophene-2-carbaldehyde (a yield of 56%).

(iv) Synthesis of Compound Represented by Chemical Formula 1-1

0.07 g (0.2 mmol) of the obtained compound (3) is suspended in ethanol, 0.04 g (0.24 mmol) of 1,3-dimethyl-2-thiobarbituric acid synthesized according to a method described in J. Pharmacol., 1944, 82, 292., P. 4417 is added thereto, and the mixture is reacted at 50° C. for 2 hours, obtaining 0.1 g of a compound represented by Chemical Formula 1-1 (a yield of 95%). The compound is sublimated and purified up to purity of 99.5%.

$^1$HNMR ppm (CDCl$_3$) 8.5 (s)-1H, 8.0 (m)-3H, 7.9 (d)-1H, 7.6 (m)-7H, 7.4 (t)-2H, 6.4 (d)-1H, 3.8 (d)-6H Synthesis Example 2: Synthesis of the Compound Represented by Chemical Formula 1-2 (5-((5-(diphenylamino)selenophen-2-yl)methylene)-1,3-dimethyl-2-thioxodihydropyrimidine-4,6(1H,5H)-dione)

[Chemical Formula 1-2]

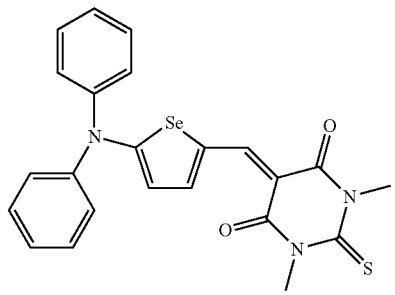

A compound represented by Chemical Formula 1-2 is obtained according to the same method as Synthesis Example 1 except for using diphenylamine instead of the 1-naphthylphenylamine. (a yield of 98%)

$^1$HNMR ppm (CDCl$_3$) 8.5 (s)-1H, 7.9 (d)-1H, 7.5-7.3 (m)-10H, 6.6 (d)-1H, 3.8 (d)-6H Synthesis Example 3: Synthesis of Compound Represented by Chemical Formula 1-3 (5-((5-(naphthalen-1-yl(phenyl)amino)selenophen-2-yl)methylene)-2-thioxodihydropyrimidine-4,6(1H,5H)-dione)

[Chemical Formula 1-3]

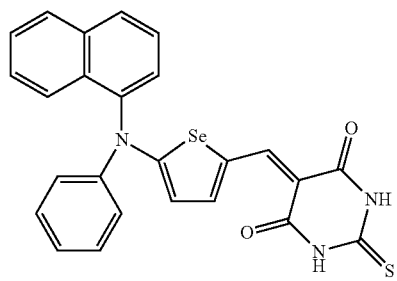

A compound represented by Chemical Formula 1-3 is obtained according to the same method as Synthesis Example 1 except for using 2-thiobarbituric acid instead of the 1,3-dimethyl-2-thiobarbituric acid. (a yield of 99%)

$^1$HNMR ppm (CDCl$_3$) 8.3 (s)-1H, 8.0 (m)-3H, 7.9 (d)-1H, 7.6 (m)-7H, 7.5 (t)-2H, 6.4 (d)-1H, 3.8 (m)-2H Synthesis Example 4: Synthesis of Compound Represented by Chemical Formula 1-4 (5-((5-(di-p-tolylamino)selenophen-2-yl)methylene)-1,3-dimethyl-2-thioxodihydropyrimidine-4,6(1H,5H)-dione)

[Chemical Formula 1-4]

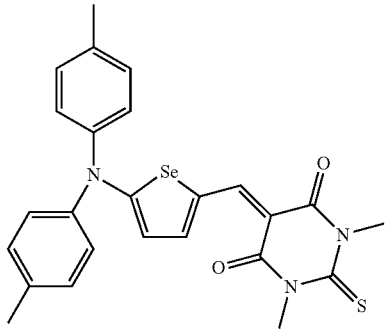

A compound represented by Chemical Formula 1-4 is obtained according to the same method as Synthesis Example 1 except for using di-p-tolylamine instead of the 1-naphthylphenylamine. (a yield of 97%)

$^1$HNMR ppm (CDCl$_3$) 8.5 (s)-1H, 7.9 (d)-1H, 7.3 (m)-8H, 6.6 (d)-1H, 3.8 (d)-6H, 2.4 (m)-6H Synthesis Example 5: Synthesis of Compound Represented by Chemical Formula 1-5 (5-((5-(diphenylamino)selenophen-2-yl)methylene)-2-thioxodihydropyrimidine-4,6(1H,5H)-dione)

[Chemical Formula 1-5]

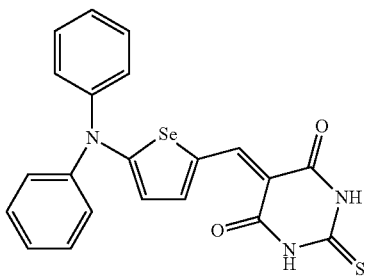

A compound represented by Chemical Formula 1-5 is obtained according to the same method as Synthesis Example 1 except for using diphenylamine instead of the 1-naphthylphenylamine and 2-thiobarbituric acid instead of the 1,3-dimethyl-2-thiobarbituric acid. (a yield of 98%)

$^1$HNMR ppm (CDCl$_3$) 8.5 (s)-1H, 7.9 (d)-1H, 7.5-7.3 (m)-10H, 6.6 (d)-1H, 3.8 (d)-2H Synthesis Example 6: Synthesis of Compound Represented by Chemical Formula 1-6 (5-((5-(bis(4-chlorophenyl)amino)selenophen-2-yl)methylene)-1,3-dimethyl-2-thioxodihydropyrimidine-4,6(1H,5H)-dione)

[Chemical Formula 1-6]

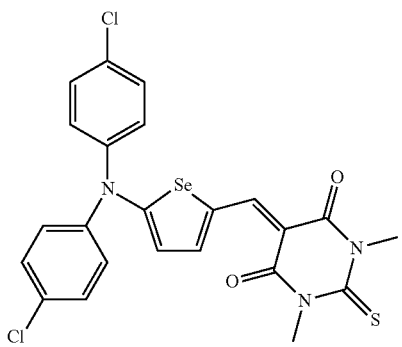

A compound represented by Chemical Formula 1-6 is obtained according to the same method as Synthesis Example 1 except for using bis(4-chlorophenyl)amine instead of the 1-naphthylphenylamine. (a yield of 97%)

$^1$HNMR ppm (DMSO-d6) 8.5 (s)-1H, 8.4 (d)-1H, 7.7 (m)-8H, 6.6 (d)-1H, 3.8 (d)-6H Synthesis Example 7: Synthesis of Compound Represented by Chemical Formula 1-7 (1,3-dimethyl-5-((5-(naphthalen-1-yl(phenyl)amino)selenophen-2-yl)methylene)-2-selenoxodihydropyrimidine-4,6(1H,5H)-dione)

[Chemical Formula 1-7]

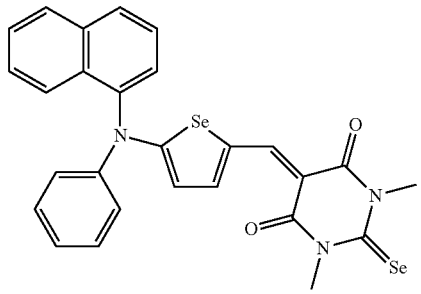

[Reaction Scheme 1-7]

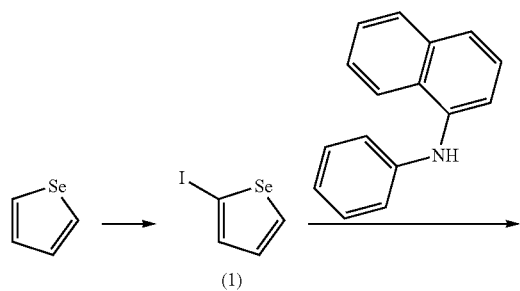

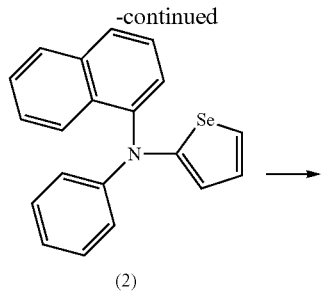

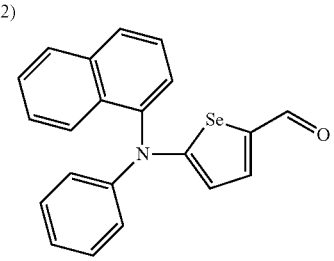

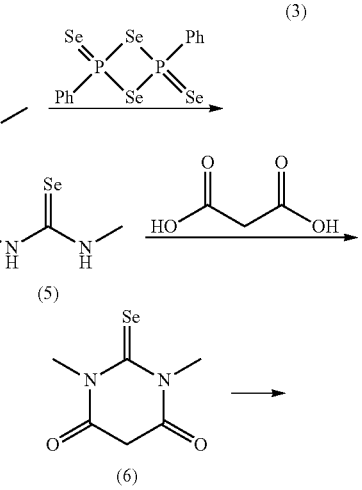

(i) Synthesis of Compound (3)

A compound (3) is synthesized according to the same method as Synthesis Example 1.

(ii) Synthesis of Compound (6)

1.31 g of a compound (5) (1,3-dimethylselenourea) (a yield of 76%) is synthesized by using 200 mg (2.27 mmol)

of 1,3-dimethylurea and 400 mg (0.75 mmol) of a woollins reagent according to a method described in Selenocarbonyl Synthesis using Woollins Reagent (Pravat Bhattacharyya; J. Derek Woollins, Tetrahedron 2001, 42, 5949-5951).

1.31 g (8.67 mmol) of the compound (5), 0.45 g (4.33 mmol) of malonic acid, and 20 ml of acetic anhydride are reacted at 90° C. for 3 hours, obtaining 5.2 g of a compound (6) (1,3-dimethyl-2-selenoxodihydropyrimidine-4,6(1H, 5H)-dione) (a yield of 60%) (J. Pharmacol., 1944, 82, 292., P. 4417).

(iii) Synthesis of Compound Represented by Chemical Formula 1-7

1 g (2.65 mmol) of the compound (3) is suspended in ethanol, 0.63 g (2.92 mmol) of the compound (6) is added thereto, and the mixture is reacted at 50° C. for 2 hours, obtaining 1.2 g of a compound represented by Chemical Formula 1-7 (a yield of 95%).

Comparative Synthesis Example 1: Synthesis of Compound Represented by Chemical Formula 1-8 (1,3-dimethyl-5-((5-(naphthalen-1-yl(phenyl)amino) thiophen-2-yl)methylene)-2-thioxodihydropyrimidine-4,6(1H,5H)-dione)

[Chemical Formula 1-8]

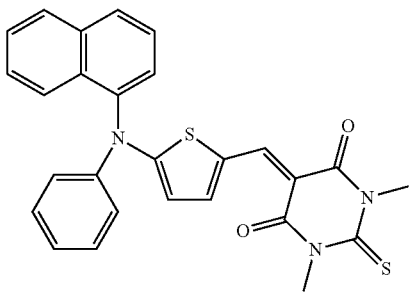

A compound represented by Chemical Formula 1-8 is obtained according to the same method as Synthesis Example 1 except for using 2-iodothiophene instead of the 2-iodoselenophene in the (i) of Synthesis Example 1. (a yield of 97%)

$^1$HNMR ppm (CDCl$_3$) 8.5 (s)-1H, 8.0 (m)-3H, 7.9 (d)-1H, 7.6 (m)-7H, 7.4 (t)-2H, 6.4 (d)-1H, 3.8 (d)-6H Light Absorption Characteristics of Compounds According to Synthesis Examples 1 to 7 and Comparative Synthesis Example 1

Light absorption characteristics (absorption wavelength, absorption intensity, and full width at half maximum (FWHM)) of the compounds according to Synthesis Examples 1 to 7 and Comparative Synthesis Example 1 depending on a wavelength are evaluated. The light absorption characteristics are evaluated in a solution state and in a thin film state.

The light absorption characteristics in the solution state are evaluated by respectively dissolving the compounds according to Synthesis Examples 1, 2, and 4 in an amount of $1.0 \times 10^{-5}$ mol/L in toluene and respectively dissolving the compounds according to Synthesis Examples 3 and 5 in an amount of $1.0 \times 10^{-5}$ mol/L in tetrahydrofuran.

The light absorption characteristics in the thin film state are evaluated by thermally evaporating each compound according to Synthesis Examples 1 to 7 and Comparative Synthesis Example 1 and C60 in a volume ratio of 1:1 under a high vacuum ($<10^{-7}$ Torr) at a speed of 0.5 to 1.0 Å/s to form a 70 nm-thick thin film and radiating an ultraviolet (UV)-visible ray (UV-Vis) with a Cary 5000 UV spectrometer (Varian Medical Systems). The results of the compounds according to Synthesis Examples 1 to 4 and Comparative Synthesis Example 1 are provided in Table 1.

TABLE 1

| | Solution | | Thin film | | |
|---|---|---|---|---|---|
| | $\lambda_{max}$ (nm) | Absorption intensity (cm$^{-1}$M$^{-1}$) | $\lambda_{max}$ (nm) | Absorption intensity (cm$^{-1}$) | FWHM (nm) |
| Synthesis Example 1 | 522 | 90000 | 529 | 77000 | 102 |
| Synthesis Example 2 | 524 | 90000 | 535 | 62000 | 110 |
| Synthesis Example 3 | 537 | 85300 | 560 | 81000 | 119 |
| Synthesis Example 4 | 526 | 86700 | 527 | 75000 | 91 |
| Comparative Synthesis Example 1 | 514 | 93700 | immeasurable | immeasurable | immeasurable |

Referring to Table 1, the compounds according to Synthesis Examples 1 to 4 exhibit a maximum absorption wavelength in a green wavelength region (e.g., at 527 nm to 560 nm in a thin film state), a narrower full width at half maximum (FWHM), and higher absorption intensity. Accordingly, the compounds according to Synthesis Examples 1 to 4 exhibit improved green wavelength selectivity. On the contrary, the compound according to Comparative Synthesis Example 1 is impossible to deposit, and thus, absorption characteristics of the compound in a thin film state are impossible to evaluate.

Thermal Stability of Compounds of Synthesis Examples 1 to 7 and Comparative Synthesis Example 1

Thermal stability of the compounds according to Synthesis Examples 1 to 7 and Comparative Synthesis Example 1 is evaluated by measuring a melting point (at an atmospheric pressure) and a deposition temperature ($T_a$). The deposition temperature indicates a temperature where a compound loses a weight of 10% through sublimation at a pressure of 10 Pa and is measured in a thermal gravimetric analysis (TGA) method. The results of the compounds according to Synthesis Examples 1 to 5 and Comparative Synthesis Example 1 are provided in Table 2.

TABLE 2

| | $T_m$ (° C.) | Deposition temperature ($T_s$, ° C.) | $\Delta T$ (° C.) ($T_m - T_s$) |
|---|---|---|---|
| Synthesis Example 1 | 251 | 244 | 7 |
| Synthesis Example 2 | 308 | 232 | 76 |
| Synthesis Example 3 | 327 | 277 | 50 |
| Synthesis Example 4 | 285 | 236 | 49 |
| Synthesis Example 5 | 344 | 278 | 66 |
| Comparative Synthesis Example 1 | 200 | 238 | −38 Non-depositable |

Referring to Table 2, the compounds according to Synthesis Examples 1 to 5 have a relatively large difference between a melting point and a deposition temperature, and accordingly, the compounds according to Synthesis Examples 1 to 5 turn out to have improved thermal stability. The compounds according to Synthesis Examples 1 to 5 have improved thermal stability and thus may be stably applied in a heat treatment process during manufacture of an organic photoelectric device, thereby improving reliability of the device. On the contrary, the compound according to Comparative Synthesis Example 1 has an undesirably small difference between a melting point and a deposition temperature, and thus, may not be deposited.

Example 1: Manufacture of Organic Photoelectric Device

An about 150 nm-thick anode is formed by sputtering ITO on a glass substrate, and an 150 nm-thick active layer is formed by codepositing the compound represented by Chemical Formula 1-1 according to Synthesis Example 1 (a p-type semiconductor compound) and C60 (an n-type semiconductor compound) in a volume ratio of 1:1. On the active layer, a molybdenum oxide ($MoO_x$, $0<x\leq3$) thin film is deposited to form a 10 nm-thick charge auxiliary layer. Subsequently, a 7 nm-thick cathode is formed by sputtering ITO on the molybdenum oxide thin film, manufacturing an organic photoelectric device.

Examples 2 to 7: Manufacture of Organic Photoelectric Device

Each organic photoelectric device according to Examples 2 to 7 is manufactured according to the same method as Example 1 except for respectively using the compounds of Synthesis Example 2 to 7 instead of the compound of Synthesis Example 1.

Comparative Example 1: Manufacture of Organic Photoelectric Device

An organic photoelectric device according to Comparative Example 1 is manufactured according to the same method as Example 1 except for using the compound of Comparative Synthesis Example 1 instead of the compound of Synthesis Example 1. However, the compound of Comparative Synthesis Example 1 is impossible to deposit, failing in manufacturing an organic photoelectric device.
External Quantum Efficiency (EQE) and Internal Quantum Efficiency (IQE) of Organic Photoelectric Devices of Examples 1 to 7

External quantum efficiency (EQE) and internal quantum efficiency (IQE) of the organic photoelectric devices according to Examples 1 to 7 depending on a wavelength and a voltage are measured.

The external quantum efficiency and the internal quantum efficiency are measured by using an IPCE measurement system (McScience Inc., Korea). First, a Si photodiode (Hamamatsu Photonics K.K., Japan) is used to calibrate the equipment, the equipment is mounted with the organic photoelectric devices according to Examples 1 to 7, and the external quantum efficiency and internal quantum efficiency of the organic photoelectric devices are measured in a wavelength range of about 350 nm to about 750 nm. The results of the organic photoelectric devices according to Examples 1 and 2 are provided in Table 3.
Color Reproducibility (ΔE*Ab) and Sensitivity (YSNR10)

An image sensor is manufactured by disposing each organic photoelectric device according to Examples 1 to 7 instead of the organic photoelectric device 100 of the image sensor 300 shown in FIG. 4.

A color difference ΔE*ab and YSNR10 are obtained when an 18% gray patch in a Macbeth chart is photographed under illumination light of D-65 and 24 colors in the Macbeth chart.

Herein, lens having an F value of 2.8 and transmittance of 80% are used, and as for an infrared ray-cut filter, general interference lens are used. An image sensor is set to have a pixel size of 1.4 μm and a frame rate of 15 fps.

The YSNR10 is obtained in a method provided in "Image Sensors and Image Quality in Mobile Phones" by Juha Alakarhu in the summary of 2007's International Image Sensor Workshop (Ogunquit Me., USA). YSNR10 values (luminance) under ΔE*ab=3.0 is obtained by calibrating a color with CCM (Color Correction Matrix). The measurement results of Example 1 and 2 are shown in Table 3.

TABLE 3

| Organic photoelectric device | EQE (%) (at −3 V) | IQE (%) (at −3 V) | Δ E *ab | YSNR10 (lux) |
| --- | --- | --- | --- | --- |
| Example 1 | 62 | 74 | 3.0 | 90 |
| Example 2 | 74 | 86 | 3.0 | 80 |

As shown in Table 3, the organic photoelectric devices according to Examples 1 and 2 exhibit improved external quantum efficiency and internal quantum efficiency.

In addition, each image sensor including the organic photoelectric devices according to Examples 1 and 2 exhibits YSNR10 of less than or equal to 90 at ΔE*ab=3.0, when color-corrected by CCM (Color Correction Matrix), which indicates that each image sensor may realize relatively high sensitivity in a pixel of relatively high image quality of 1.4 μm.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:
1. A compound for an organic photoelectric device represented by the following Chemical Formula 1:

[Chemical Formula 1]

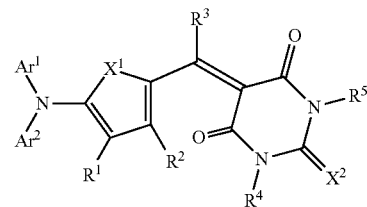

wherein, in Chemical Formula 1,
$X^1$ is one of Se, Te, S(=O), S(=O)$_2$, and $SiR^aR^b$, wherein each of $R^a$ and $R^b$ is one of hydrogen and a $C_1$ to $C_{10}$ alkyl group,
$X^2$ is one of O, S, Se, Te, and C($R^c$)(CN), wherein $R^c$ is one of hydrogen, a cyano group (—CN), and a $C_1$ to $C_{10}$ alkyl group,
each of $Ar^1$ and $Ar^2$ is independently one of a substituted or unsubstituted $C_6$ to $C_{30}$ aryl group and a substituted or unsubstituted $C_4$ to $C_{30}$ heteroaryl group, and
each of $R^1$ to $R^5$ is independently one of hydrogen, deuterium, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof.

2. The compound of claim 1, wherein each of the $Ar^1$ and $Ar^2$ is independently one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

3. The compound of claim 1, wherein at least one of the $Ar^1$ and $Ar^2$ is one of a substituted or unsubstituted naphthyl group, a substituted or unsubstituted anthracenyl group, a substituted or unsubstituted phenanthrenyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

4. The compound of claim 1, wherein the compound has a maximum absorption wavelength ($\lambda_{max}$) of about 500 nm to about 600 nm in a thin film state.

5. The compound of claim 1, wherein the compound has a maximum absorption wavelength ($\lambda_{max}$) of about 525 nm to about 560 nm in a thin film state.

6. The compound of claim 1, wherein the compound exhibits a light absorption curve having a full width at half maximum (FWHM) of about 50 nm to about 120 nm in a thin film state.

7. The compound of claim 1, wherein a difference between a melting point and a deposition temperature of the compound is greater than or equal to about 5° C.

8. The compound of claim 1, wherein a difference between a melting point and a deposition temperature of the compound is greater than or equal to about 30° C.

9. The compound of claim 1, wherein a difference between a melting point and a deposition temperature of the compound is greater than or equal to about 50° C.

10. An organic photoelectric device comprising:
a first electrode and a second electrode facing each other, and
an active layer between the first electrode and the second electrode, the active layer including the compound represented by Chemical Formula 1:

[Chemical Formula 1]

wherein, in Chemical Formula 1,
$X^1$ is one of Se, Te, S(=O), S(=O)$_2$, and SiR$^a$R$^b$, wherein each of R$^a$ and R$^b$ is one of hydrogen and a $C_1$ to $C_{10}$ alkyl group,
$X^2$ is one of O, S, Se, Te, and C(R$^c$)(CN), wherein R$^c$ is one of hydrogen, a cyano group (—CN), and a $C_1$ to $C_{10}$ alkyl group,
each of $Ar^1$ and $Ar^2$ is independently one of a substituted or unsubstituted $C_6$ to $C_{30}$ aryl group and a substituted or unsubstituted $C_4$ to $C_{30}$ heteroaryl group, and
each of $R^1$ to $R^5$ is independently one of hydrogen, deuterium, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and combination thereof.

11. The organic photoelectric device of claim 10, wherein each of the $Ar^1$ and $Ar^2$ is independently one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

12. The organic photoelectric device of claim 10, wherein at least one of the $Ar^1$ and $Ar^2$ is one of a substituted or unsubstituted naphthyl group, a substituted or unsubstituted anthracenyl group, a substituted or unsubstituted phenanthrenyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

13. The organic photoelectric device of claim 10, wherein the active layer has a maximum absorption wavelength ($\lambda_{max}$) of about 500 nm to about 600 nm.

14. The organic photoelectric device of claim 10, wherein the active layer has a maximum absorption wavelength ($\lambda_{max}$) of about 525 nm to about 560 nm.

15. The organic photoelectric device of claim 10, wherein the active layer exhibits a light absorption curve having a full width at half maximum (FWHM) of about 50 nm to about 120 nm.

16. The organic photoelectric device of claim 10, wherein a difference between a melting point and a deposition temperature of the compound is greater than or equal to about 5° C.

17. An image sensor comprising the organic photoelectric device of claim 10.

18. The image sensor of claim 17, further comprising:
a semiconductor substrate integrated with a plurality of first photo-sensing devices configured to sense light in a blue wavelength region and a plurality of second photo-sensing devices configured to sense light in a red wavelength region,
wherein the organic photoelectric device is on the semiconductor substrate and is configured to selectively absorb light in a green wavelength region.

19. The image sensor of claim 18, wherein the first photo-sensing devices and the second photo-sensing devices are stacked in a vertical direction on the semiconductor substrate.

20. The image sensor of claim 18, further comprising:
a color filter layer between the semiconductor substrate and the organic photoelectric device, the color filter layer including a blue filter configured to selectively transmit light in a blue wavelength region and a red filter configured to selectively transmit light in a red wavelength region.

21. The image sensor of claim 17, wherein
the organic photoelectric device is a green photoelectric device, and
the image sensor includes the green photoelectric device, a blue photoelectric device configured to selectively absorb light in a blue wavelength region, and a red photoelectric device configured to selectively absorb light in a red wavelength region which are stacked.

22. An electronic device comprising the image sensor of claim 17.

23. An active layer comprising a compound for an organic photoelectric device having a melting point higher than a deposition temperature of the compound, the compound represented by the following Chemical Formula 1:

[Chemical Formula 1]

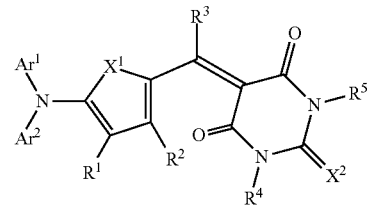

wherein, in Chemical Formula 1, $X^1$ is one of Se, Te, S(=O), S(=O)$_2$, and SiR$^a$R$^b$, wherein each of R$^a$ and R$^b$ is one of hydrogen and a $C_1$ to $C_{10}$ alkyl group, $X^2$ is one of O, S, Se, Te, and C(R$^c$)(CN), wherein R$^c$ is one of hydrogen, a cyano group (—CN), and a $C_1$ to $C_{10}$ alkyl group, each of Ar$^1$ and Ar$^2$ is independently one of a substituted or unsubstituted $C_6$ to $C_{30}$ aryl group and a substituted or unsubstituted $C_4$ to $C_{30}$ heteroaryl group, and each of R$^1$ to R$^5$ is independently one of hydrogen, deuterium, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof.

* * * * *